(12) United States Patent
Given

(10) Patent No.: US 7,628,790 B2
(45) Date of Patent: Dec. 8, 2009

(54) METHOD OF TREATING SPIDER VEINS

(76) Inventor: Kenna S. Given, 748 Tripps Ct., Augusta, GA (US) 30909

( * ) Notice: Subject to any disclaimer, the term of this patent is extended or adjusted under 35 U.S.C. 154(b) by 455 days.

(21) Appl. No.: 11/537,739

(22) Filed: Oct. 2, 2006

(65) Prior Publication Data

US 2007/0038212 A1  Feb. 15, 2007

Related U.S. Application Data

(63) Continuation of application No. 10/243,818, filed on Sep. 13, 2002, now Pat. No. 7,125,406.

(51) Int. Cl.
*A61B 18/14* (2006.01)
(52) U.S. Cl. ............................. 606/49; 606/41; 606/50
(58) Field of Classification Search ................. 606/41, 606/45, 49, 32, 1, 50, 27, 28; 128/898; 600/381, 600/490, 505, 36
See application file for complete search history.

(56) References Cited

U.S. PATENT DOCUMENTS 6,413,255 B1 * 7/2002 Stern ........................... 606/41
2001/0029373 A1 * 10/2001 Baker et al. ................... 606/49
2002/0165529 A1 * 11/2002 Danek .......................... 606/28

* cited by examiner

*Primary Examiner*—Roy D Gibson
(74) *Attorney, Agent, or Firm*—Bryan W. Bockhop; Bockhop & Associates, LLC

(57) ABSTRACT

An electrocautery instrument in accordance with the present invention facilitates a relatively non-invasive procedure for treating small varicose and spider veins. In the furtherance of this and other objectives, an electrocautery device is provided that does not have to be inserted or into the veins in order to satisfactorily treat them. In particular, an exemplary electrocautery instrument can destroy the target tissue when brought into with the target vein. Moreover, the electrocautery instrument can destroy target veins without causing collateral damage to neighboring tissue. In the furtherance of this and other objectives a thin sheath of biocompatible material coats substantially the entire needle portion of the electrocautery instrument so as to prevent the exposure of neighboring tissue to its therapeutics. The sheath effectively shields surrounding tissue from exposure, while being sufficiently thin to allow for unobstructed insertion of the needle through the skin of a patient to the target site.

8 Claims, 3 Drawing Sheets

METHOD OF TREATING SPIDER VEINS

CROSS-REFERENCE TO RELATED APPLICATION(S)

This application is a continuation of, and claims the benefit of, U.S. patent application Ser. No. 10/243,818, filed Sep. 13, 2002 now U.S. Pat. No. 7,125,406, the entirety of which is hereby incorporated herein by reference.

BACKGROUND OF THE INVENTION

1. Field of the Invention

The present invention relates generally to electrical equipment and an electrocautery instrument in particular.

2. Description of the Prior Art

Varicose veins are blood vessels that have become twisted and swollen when their one-way valves are compromised or when the vein wall weakens. As people grow older, the likelihood of having large and/or smaller varicose and spider veins increases. In fact, varicose and spider veins affect over half the population by age 55 and is linked to factors such as heredity, pregnancy, estrogen medications, prolonged standing or sitting, sedentary lifestyle, and injury to the legs. Left untreated, varicose veins can cause pain, swelling, phlebitis, chronic skin ulcers, and potentially life-threatening blood clots. Unsightly and embarrassing spider veins, on the other hand, are not dangerous and are simply enlarged venules.

Though benign, many individuals desire treatment of spider veins because of their appearance. Traditional treatment has consisted of sclerotherapy, which involves injecting a small amount of a mild sclerosing solution into the affected veins. Many different kinds of chemical solutions have been used for this purpose, including hypersonic sodium chloride, sodium morrhuate, sodium tetradecyl sulfate, polilocanol, sclerodex-dextroject, chromated glycerin and polyiodide Iodine to name a few. Treated veins gradually disappear over one to six months. It frequently takes several sessions to provide the most effective results. Unfortunately, sclerotherapy treatments are not effective for larger varicose veins, which require more aggressive treatment.

Another approach is to obliterate the spider veins directly with the laser. Although this treatment can be successful, there is a significant risk of scarring. In addition, the equipment is very expensive.

Therefore, there exists a need for a relatively inexpensive non-invasive procedure for treating spider veins. Moreover, there is an existing need for a device that can destroy the target veins without causing collateral damage to neighboring tissue.

SUMMARY OF THE INVENTION

The advantages of an improve electrocautery instrument are numerous. In particular, an electrocautery instrument in accordance with the present invention provides precision in that the user can be assured of site-specific results without collateral tissue damage. The present invention comprises an electrocautery needle with an insulated shaft and beveled tip and a special connector that connects the needle to an electrosurgical generator.

A principal advantage of an electrocautery instrument in accordance with the present invention is that the device facilitates a simple procedure for treating spider veins. An additional objective is to provide an electrocautery instrument that can destroy the target veins without causing collateral damage to neighboring tissue. Yet another objective of a preferred embodiment in accordance with the present invention is to provide an electrocautery instrument that has a narrow working diameter for introduction through the dermis of a patient. In the furtherance of this and other objectives, an electrocautery instrument is provided that has a biocompatible sheath that does not exceed 0.0005" while still providing protection from collateral damage.

The various features of novelty, which characterize the invention, are pointed out with particularity in the claims annexed to and forming a part of this disclosure. For a better understanding of the invention, its operating advantages and specific objects attained by its use, reference should be made to the accompanying drawings and descriptive matter in which there are illustrated and described the preferred embodiments of the invention, like reference numerals or letters signifying the same or similar components.

DETAILED DESCRIPTION OF THE INVENTION

Electrocautery techniques traditionally consist of a device in which an electric current is used to heat a treatment instrument or probe. The heated probe cauterizes vessels, thus minimizing blood loss during surgery. Also called thermal cautery, this device does not transfer any electric current to the patient.

The advantages of an improved electrocautery tip are numerous. In particular, an electrocautery instrument in accordance with the present invention provides precision in that the user can be assured of site-specific results without collateral tissue damage.

Though the tip of the electrocautery instrument may not necessarily be introduced into the target vein, nonspecific collateral tissue damage is minimized as a result of the design of the electrosurgical tip. The tip preferably comprises a needle with a preferred diameter of about 0.01 and coated with a biocompatible sheath. The necessary characteristic of an acceptable sheath is that it adequately serves as a protective layer that does not inhibit insertion of the tip effectively through the dermis of a patient. In particular, the sheath has a thickness of equal to or less than 0.0005". Moreover, at this preferred thickness the sheath must not only allow adequate tip insertion but must also provide protection to tissue around the target vein.

The ability of the electrocautery instrument to destroy target veins without causing collateral damage to neighboring tissue is a function of the thickness of the sheath as well as the location of the sheath. The sheath of biocompatible material coats substantially the entire needle portion of the electrocautery needle so as to prevent the exposure of neighboring tissue to its therapeutics.

Figure 1:
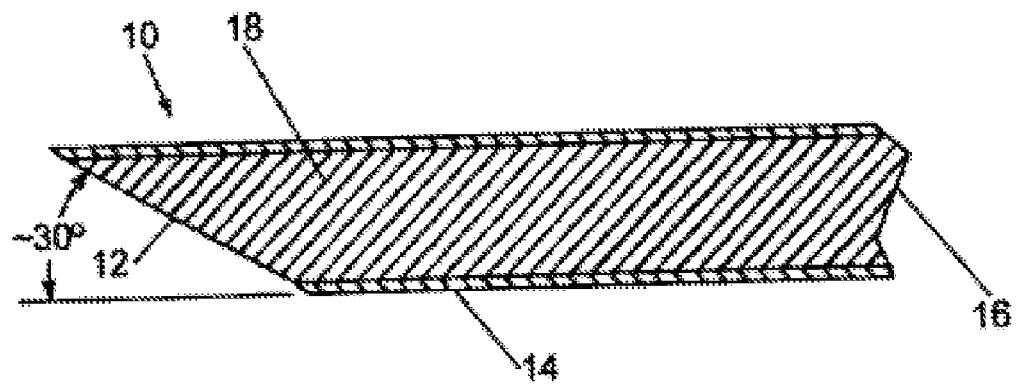
FIG. 1 is a side cross sectional view of the electrosurgical tip of an exemplary electrocautery instrument in accordance with the invention.

Referring now to the FIG. 1, an exemplary electrosurgical needle 10 for an electrocautery instrument is provided that comprises an exposed tip 12, where the needle 10 is substantially covered by a biocompatible sheath 14. Unlike conventional devices where electrode insulation terminates short of its tip, the needle 10 in accordance with the present invention is substantially coterminous with the tip. In a preferred embodiment, the tip 12 of needle 10 is beveled to insure that the maximum surface area is coated by the sheath 14 and preventing collateral tissue damage. The needle 10 is adapted to attach at end 16 to a standard electrocautery unit.

Figure 2:
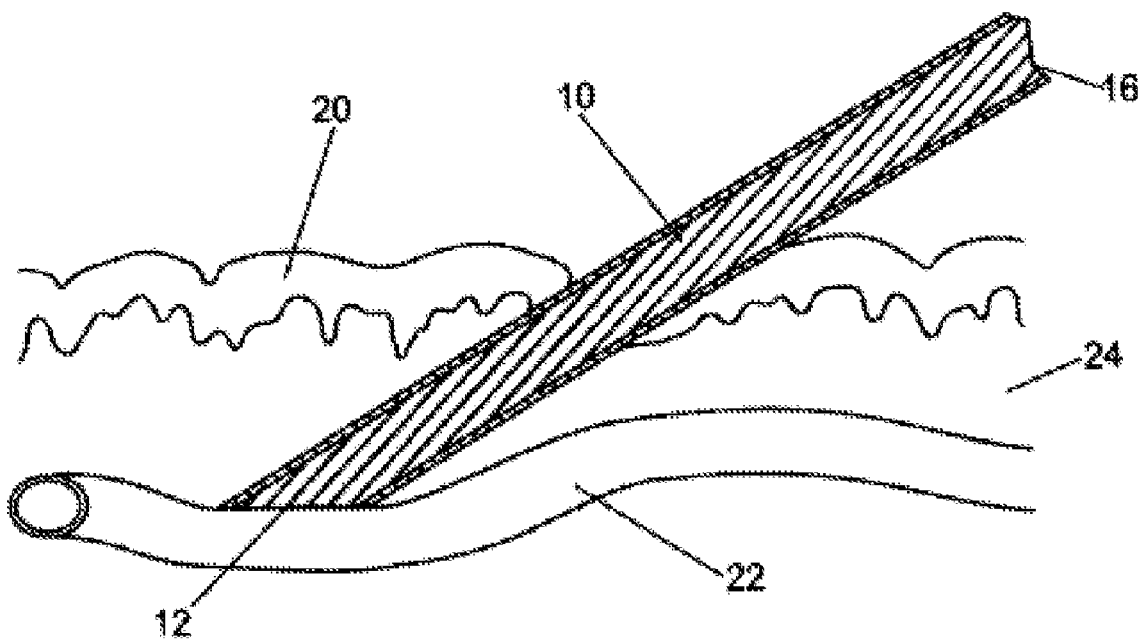
FIG. 2 is a schematic plan view of a an electrocautery instrument in accordance with a preferred embodiment of the present invention showing the electrosurgical tip within the preferable efficacious range with respect to the target vein.

FIG. 2 shows an exemplary electrosurgical needle 10, in accordance with the present invention, as inserted through the epidermis 20 and into the dermis 24 of a patient. In practice, the tip 12 of the electrosurgical needle 10 does not have to be inserted into the lumen of the target capillary 22. The tip 12 is preferably beveled to provide additional accuracy and control. An exemplary tip 12 is beveled at a 30° angle but other acute angles are acceptable. Effective treatment is achieved when the electrocautery instrument in accordance with the present invention is operated at a preferable frequency between 1.0 MHz to 1.5 MHz.

Figure 3:
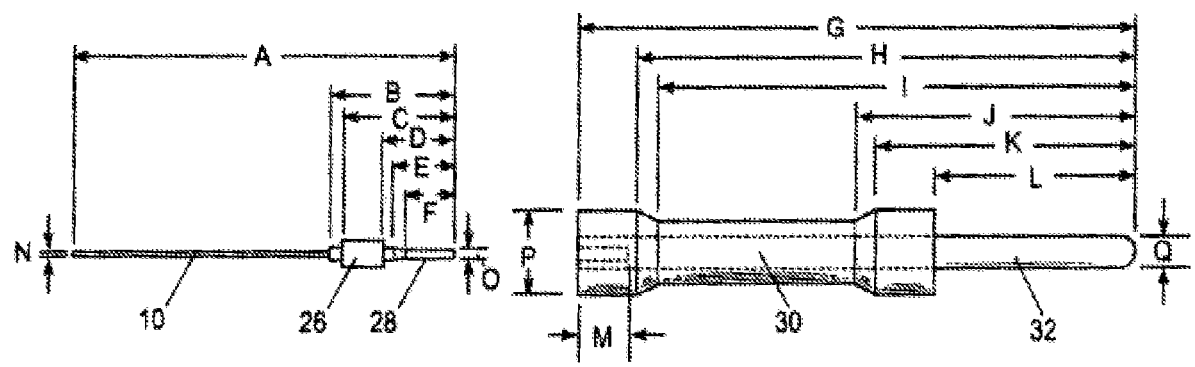
FIG. 3 is a side exploded view of the functional unit of an exemplary electrocautery instrument in accordance with the invention.
Figure 4:
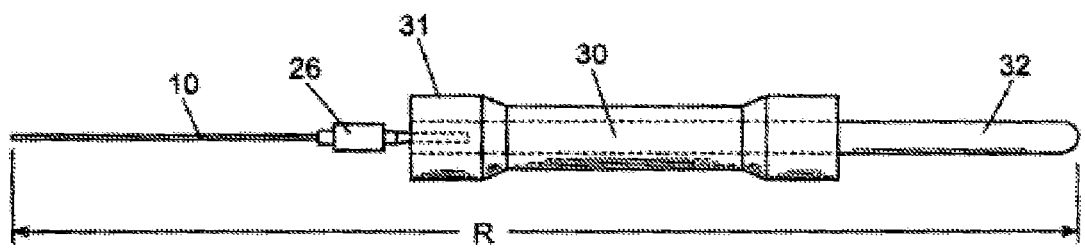
FIG. 4 is a side perspective view of the functional unit of the electrocautery instrument as shown in FIG. 3.
Figure 5:
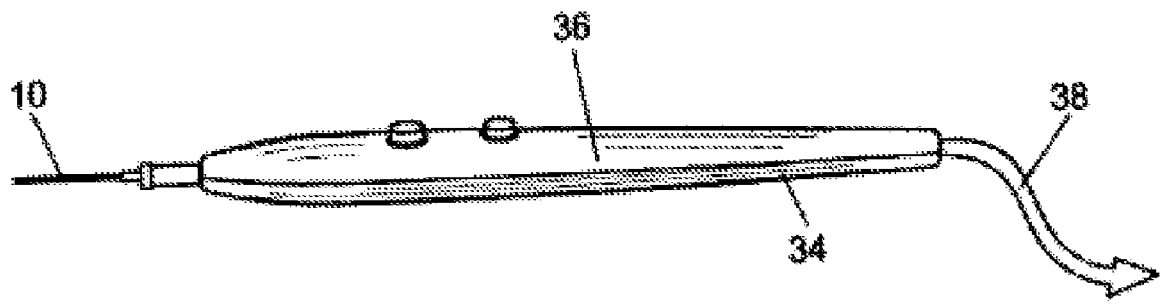
FIG. 5 is a perspective view of the functional unit installed in the handpiece of an exemplary electrocautery instrument in accordance with the invention.
Figure 6:
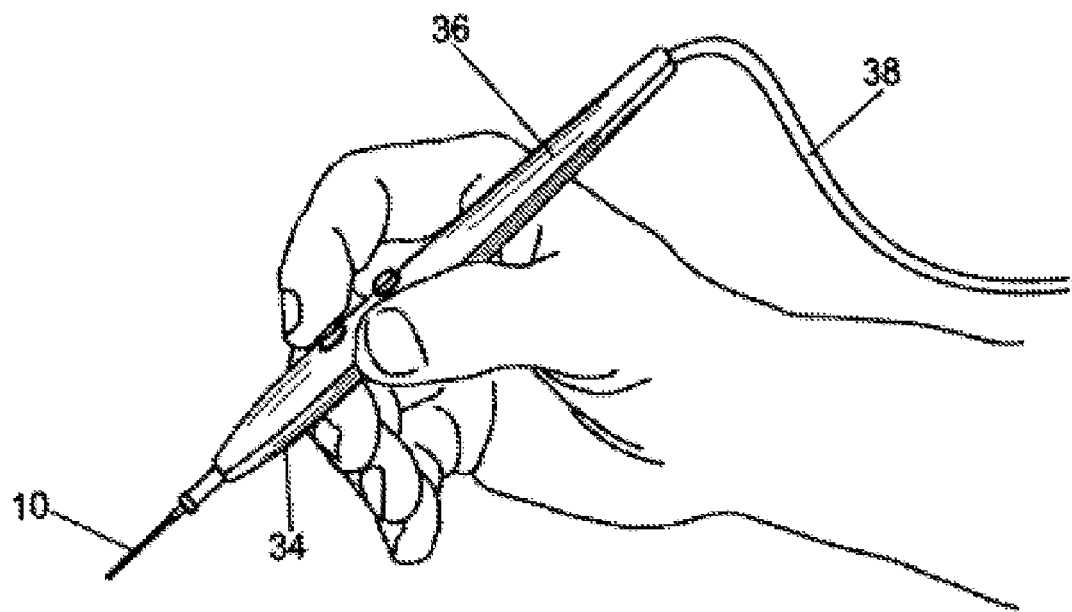
FIG. 6 is a schematic plan view of an electrocautery instrument handpiece, in the hand of a user, in accordance with a preferred embodiment of the present invention.

Referring now to FIG. 3, the functional unit 30 of an electrocautery instrument in accordance with the present invention comprises a replaceable needle 20 having an exposed tip 12 on the working end and a coupling member 28 for operatively and reversibly affixing the needle 10 with the base 31 of the functional member 30. The pieces of the functional unit 30, may be coupled together by various conventional means, including but not limited to, snap fitting, threaded mating, male/female connectors, etc. The functional unit 30 is coupled to an electrosurgical generator via cord 38 that is coupled to the terminal section 32 of the functional unit.

The following is a list of preferred dimensions for functional unit 30, where the distances for lettered regions indicated on FIG. 3 are approximated in millimeters and correspond as follows:

| | |
|---|---|
| A = | 31.5 |
| B = | 10.5 |
| C = | 9.5 |
| D = | 6.0 |
| E = | 5.0 |
| F = | 4.0 |
| G = | 47.0 |
| H = | 42.0 |
| I = | 40.0 |
| J = | 24.0 |
| K = | 22.0 |
| L = | 18.0 |
| M = | 4.5 |
| N = | 0.3 |
| O = | 0.8 |
| P = | 6.0 |
| Q = | 2.3 |
| R = | 75.0 |

It should be kept in mind that these dimensions are suggested guidelines and should not be construed as limiting if other dimensions would fulfill the objectives of the present invention.

A preferred electrocautery instrument in accordance with the present invention comprises an electrosurgical generator; a longitudinally extending functional unit having first and second ends; the first end of the functional unit operably coupled with the electrosurgical generator and configured to receive electrosurgical current from the electrosurgical generator; the second end of the functional unit terminating with an electrically conductive needle tip for administering the current derived from the electrosurgical generator and a biocompatible sheath that is substantially co-terminal with the conductive tip of the needle. In a preferred aspect in accordance with the present invention, the electrosurgical generator provides a desirable level of electrical current to the tip of the instrument. Though the desired frequency may be above 1.5 MHz, the present invention is suitably configured to adequately address varies at about between 1.0 MHz and 1.5 MHz.

The electrocautery instrument in accordance with the present invention is adaptable for indication in a variety of protocols. In a preferred embodiment, however, an exemplary electrocautery instrument can be used to treat vein abnormalities in a patient, by providing an electrocautery instrument; the specially designed tip of the instrument penetrates the skin of the patient. The tip preferably comprises an electrically conductive needle tip, which is advanced adjacent to a target vein to be treated. Once the tip is brought within contact of the target vessel, the electrosurgical generator is activated until the vein adjacent the active tip portion is damaged. Afterwards, as with other procedures, the natural regenerative processes of the patient will clear the unsightly veins after the procedure is completed. Unlike other devices that require (1) the insertion of the electrically charged tip be inserted into the vein; (2) an outer sheath with a thickness greater than 0.0006 inches and/or (3) that the sheath terminates short of the device tip, the present invention gives the user more control and causes less collateral damage. These favorable characteristics result from the fact that the present instrument does not have to be introduced into the vein, the insulation sheath is thinner (between about 0.0001-0.0005 inches) and is substantially co-terminal with the beveled tip.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

What is claimed is:

1. A method of treating a spider vein having an outer surface, comprising the steps of:
   a. applying to the outer surface of the spider vein a vein contact surface of an elongated needle, wherein the elongated needle terminates in the vein contact surface, the vein contact surface being flat and at an acute angle relative to the elongated surface, and wherein an insulating sheath completely covers the elongated needle except for the vein contact surface so that no tissue surrounding the outer surface of the spider vein is in contact with the vein contact surface; and
   b. applying an electrosurgical current to the elongated needle.

2. The method of claim 1, wherein the step of applying an electrosurgical current comprises applying a current at a frequency of not less than 1.0 MHz and not greater than 3.0 MHz.

3. The method of claim 1, further comprising the step of positioning the elongated needle so that substantially the entire vein contact surface is in contact with the outer surface of the spider vein.

4. The method of claim 3, wherein the step of positioning the elongated needle comprises holding the elongated needle at an angle of substantially 30° to the spider vein.

5. The method of claim 1, wherein the insulating sheath has a thickness of no greater than 0.0005 inches.

6. A method of treating a spider vein disposed under a patient's epidermis and having an outer surface, comprising the steps of:
   a. inserting an elongated needle through the epidermis so that a vein contact surface of the elongated needle is in contact with the outer surface of the vein, wherein the elongated needle terminates in the vein contact surface in which the vein contact surface is flat and at an acute angle relative to the elongated needle and wherein an insulating sheath completely covers the elongated needle except for the vein contact surface so that no tissue surrounding the outer surface of the spider vein is in contact with the vein contact surface; and
   b. applying an electrosurgical current to the elongated needle so that the current flows from the vein contact surface to the spider vein.

7. The method of claim 6, further comprising the step of positioning the elongated needle so that substantially the entire vein contact surface is in contact with the outer surface of the spider vein.

8. The method of claim 7, wherein the step of positioning the elongated needle comprises holding the elongated needle at an angle of substantially 30° to the spider vein.

* * * * *